(12) United States Patent
Ra (10) Patent No.: US 10,596,320 B2
(45) Date of Patent: Mar. 24, 2020

(54) FILTERING INJECTION NEEDLE ASSEMBLY FOR SYRINGE

(71) Applicant: Yong-Kuk Ra, Seoul (KR)

(72) Inventor: Yong-Kuk Ra, Seoul (KR)

(*) Notice: Subject to any disclaimer, the term of this patent is extended or adjusted under 35 U.S.C. 154(b) by 195 days.

(21) Appl. No.: 15/576,130

(22) PCT Filed: Mar. 3, 2016

(86) PCT No.: PCT/KR2016/002121
§ 371 (c)(1),
(2) Date: Nov. 21, 2017

(87) PCT Pub. No.: WO2016/190526
PCT Pub. Date: Dec. 1, 2016

(65) Prior Publication Data
US 2018/0133404 A1    May 17, 2018

(30) Foreign Application Priority Data

May 23, 2015  (KR) .................. 10-2015-0072268
Jul. 6, 2015   (KR) .................. 10-2015-0096094

(51) Int. Cl.
*A61M 5/31*     (2006.01)
*A61M 5/32*     (2006.01)
(Continued)

(52) U.S. Cl.
CPC ........ *A61M 5/3145* (2013.01); *A61M 5/1782* (2013.01); *A61M 5/31* (2013.01);
(Continued)

(58) Field of Classification Search
CPC .... A61M 5/3145; A61M 5/1782; A61M 5/31; A61M 5/32; A61M 2005/3114;
(Continued)

(56) References Cited

U.S. PATENT DOCUMENTS 3,650,093 A * 3/1972 Rosenberg .......... A61M 1/0005
                                                      604/123
4,180,071 A * 12/1979 Oiwa ...................... A61M 5/32
                                                      604/190
(Continued)

FOREIGN PATENT DOCUMENTS

KR    10-2012-0087587    8/2012
KR       10-1243396      3/2013
(Continued)

OTHER PUBLICATIONS

International Search Report for International Application No. PCT/KR2016/002121, dated Jun. 9, 2016.
(Continued)

*Primary Examiner* — Nilay J Shah
(74) *Attorney, Agent, or Firm* — LRK Patent Law Firm (57) ABSTRACT

The present invention relates to a filtering injection needle assembly for a syringe, and more particularly, to an apparatus for further facilitating suction of an injection liquid. The filtering injection needle assembly includes an injection needle (100) including a needle (110) and a hub (120); and a cap (200) configured to receive the needle (110) and including a filter (210), wherein the hub (200) is formed with a through-hole (121) for communication between an inside and an outside of the hub, and opening/closing of the through-hole (121) is controlled by a one-way valve means (300). The filtering injection needle assembly blocks foreign substances introduced into the syringe, thereby enhancing safety, and wherein the filtering injection needle assembly has various types of one-way valve means provided in the hub of the injection needle to further facilitate the suction of the injection liquid.

10 Claims, 10 Drawing Sheets

(51) Int. Cl.

| | |
|---|---|
| *A61M 5/178* | (2006.01) |
| *A61J 1/20* | (2006.01) |
| *A61M 25/00* | (2006.01) |
| *A61M 5/34* | (2006.01) |
| *A61M 5/165* | (2006.01) |
| *A61M 39/22* | (2006.01) |
| *A61M 39/24* | (2006.01) |

(52) U.S. Cl.
CPC ............ *A61M 5/32* (2013.01); *A61M 5/3202* (2013.01); *A61M 5/3293* (2013.01); *A61J 1/2079* (2015.05); *A61J 1/2086* (2015.05); *A61M 5/165* (2013.01); *A61M 5/34* (2013.01); *A61M 39/22* (2013.01); *A61M 39/24* (2013.01); *A61M 2005/3128* (2013.01); *A61M 2025/0076* (2013.01)

(58) Field of Classification Search
CPC .... A61M 5/34; A61M 5/3202; A61M 5/3293; A61M 2005/3128; A61M 5/165; A61M 2005/1652; A61M 2005/1655; A61M 2005/1657; A61M 5/3213; A61M 5/38; A61M 5/385; A61M 2025/0076; A61M 39/22; A61M 39/24; A61M 2039/248; A61M 2039/2426; A61J 1/2096; A61J 1/2086; A61J 1/2079
See application file for complete search history.

(56) References Cited

U.S. PATENT DOCUMENTS 4,332,249 A * 6/1982 Joslin ................ A61M 5/3145
                                                                  604/36
8,480,645 B1 * 7/2013 Choudhury ......... A61M 5/3297
                                                                 604/405

FOREIGN PATENT DOCUMENTS

| KR | 10-2013-0139807 | 12/2013 |
| KR | 10-1358936 | 2/2014 |
| KR | 10-1435898 | 9/2014 |
| KR | 10-1563723 | 10/2015 |

OTHER PUBLICATIONS

English translation of the Written Opinion of International Application No. PCT/KR2016/002121, dated Nov. 28, 2017.

* cited by examiner

FIG. 1

Prior Art

FIG. 2

Prior Art

FIG. 3

Prior Art

FILTERING INJECTION NEEDLE ASSEMBLY FOR SYRINGE

TECHNICAL FIELD

The present invention relates to a filtering injection needle assembly for a syringe, and more particularly, to an apparatus for further facilitating suction of an injection liquid when a cap provided with a filter for filtering a foreign substance is used on a syringe, wherein the apparatus blocks foreign substances introduced into the syringe and also adhered to an injection needle so that the apparatus may prevent ampoule fragments from being injected together with the injection liquid into a human body, thereby enhancing safety, and wherein the apparatus has various types of one-way valve means provided in a hub of the injection needle to further facilitate the suction of the injection liquid, thereby improving user's convenience of use and thus maximizing merchantability and market competitiveness of a product.

BACKGROUND ART

In general, a syringe is an instrument for injecting a liquid medicine into a body of an animal/plant and is configured to pierce a skin with a sharp tip thereof to allow the liquid medicine to be injected into any tissue of the body.

Figure 1:
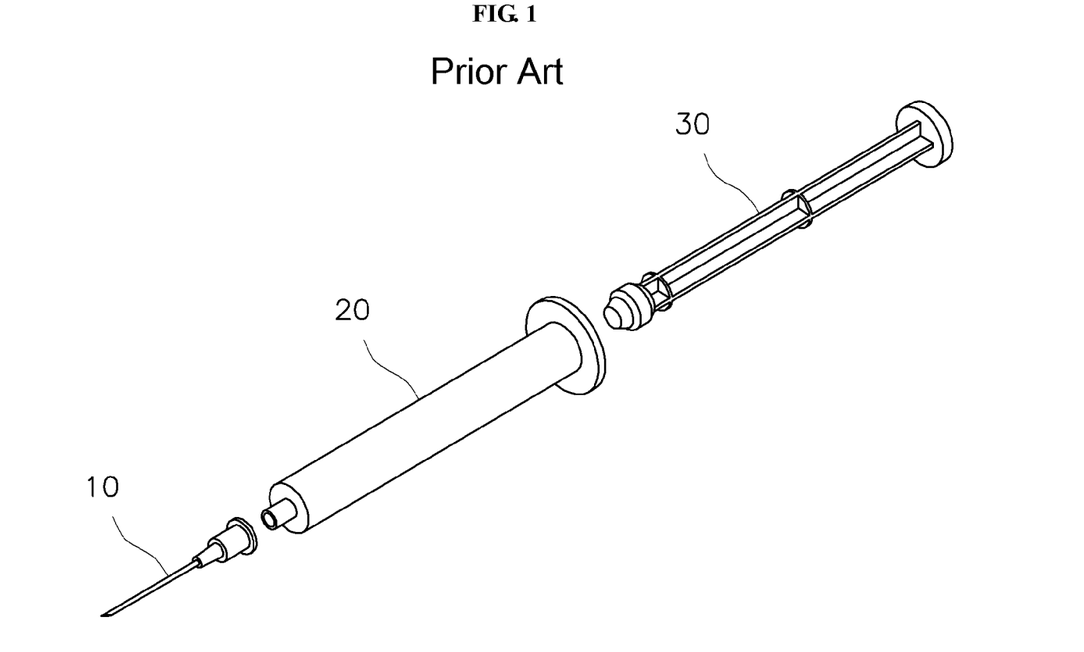
FIG. 1 is an exploded perspective view illustrating a conventional syringe.

FIG. 1 is an exploded perspective view illustrating a conventional syringe. As shown in FIG. 1, the syringe generally includes a cylinder 20 to which an injection needle 10 is coupled and in which an injection liquid is contained, and a plunger 30 provided in the cylinder 20 so as to be movable forward and backward in an axial direction.

In this conventional syringe, as the plunger 30 is retreated, a negative pressure is generated in the cylinder 20 and the cylinder 20 is then filled with an injection liquid. As the plunger 30 is moved forward, the injection liquid in the cylinder 20 is discharged through the injection needle 10 by a positive pressure and then injected into a patient's body.

However, when this conventional syringe is used, there is concern that foreign substances incorporated in the injection liquid itself or foreign substances such as glass particles scattered into and mixed with the injection liquid during a process of breaking and opening an ampoule in which the injection liquid is stored may be injected together with the injection liquid into the patient's body.

To solve this problem, a filtering syringe provided with a filter for filtering foreign substances contained in an injection liquid has been developed.

First, as disclosed in Korean Patent Laid-Open Publication No. 2012-87587, a conventional filtering syringe in which a filter for filtering foreign substances is provided in an injection needle or a cylinder performs a function of filtering foreign substances from an injection liquid suctioned into the cylinder.

However, since foreign substances had been stuck to an outer surface of the injection needle introduced into an ampoule when the injection liquid is suctioned, or foreign substances incorporated in the injection liquid remaining within the injection needle had not been filtered, it was impossible to fundamentally prevent the foreign substances from being injected together with the injection liquid into a patient's body.

In response thereto, U.S. Pat. No. 4,180,071 discloses an example in which a filter for filtering foreign substances is provided in a cap for covering an injection needle.

Figure 2:
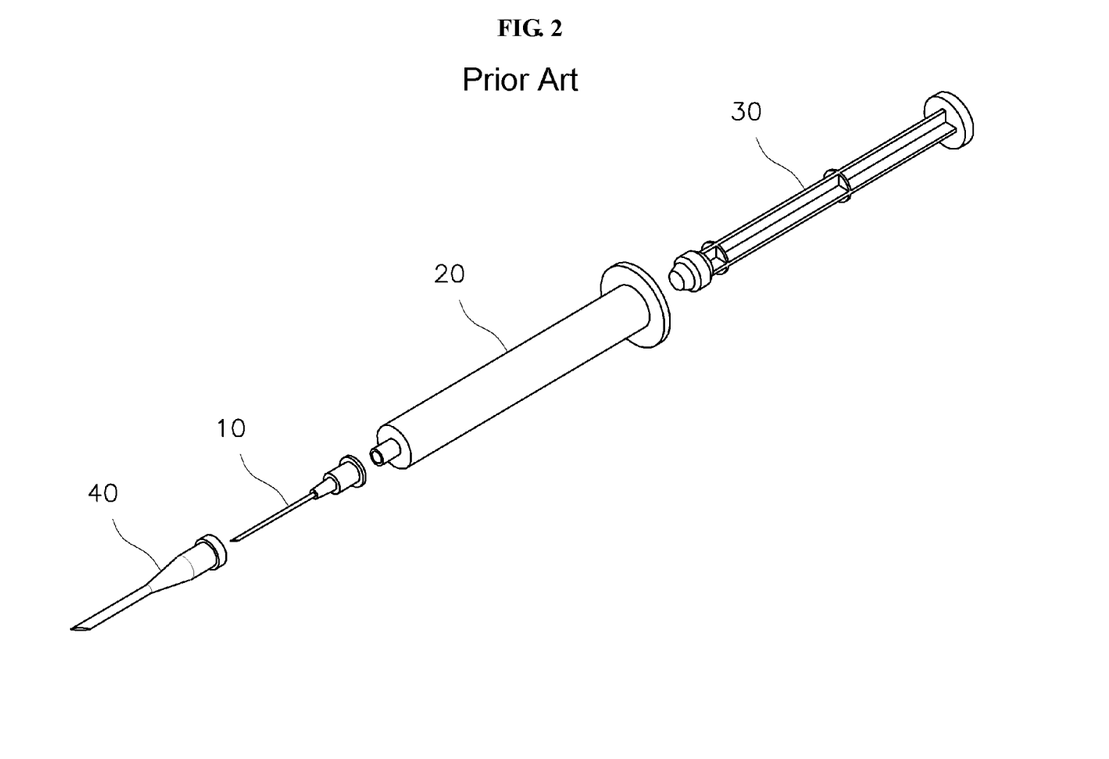
FIG. 2 is an exploded perspective view illustrating a conventional filter-cap syringe.
Figure 3:
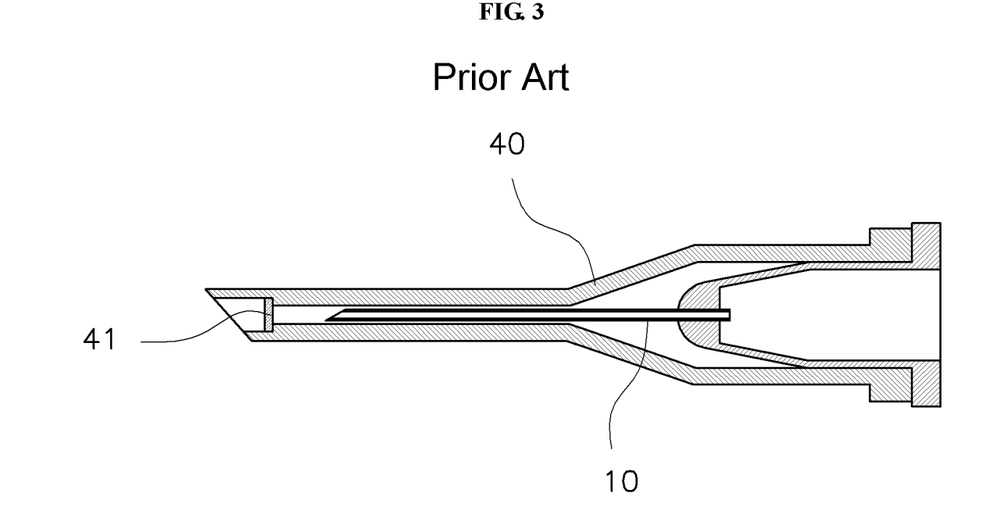
FIG. 3 is a sectional view illustrating a main portion of the conventional filter-cap syringe.

FIG. 2 is an exploded perspective view illustrating a conventional filter-cap syringe, and FIG. 3 is a sectional view illustrating a main portion of the conventional filter-cap syringe, wherein FIGS. 2 and 3 illustrate the conventional filter-cap syringe disclosed in U.S. Pat. No. 4,180,071.

Since the conventional filter-cap syringe has a filter 41 provided in a cap 40 as shown in FIG. 3 so that foreign substances are filtered by the filter 41 when an injection liquid is suctioned, and the cap 40 including the filter 41 is detached from an injection needle 10 upon injection of the injection liquid, there is no concern that foreign substances may be injected.

However, the conventional filter-cap syringe has a technical problem in that since the injection liquid can be suctioned into a cylinder 20 only via the minute injection needle 10 after passing through the filter 41 provided in the cap 40, a relatively large force is required for suctioning the injection liquid and thus it is very inconvenient to use the syringe.

PRIOR ART DOCUMENT

Korean Patent Laid-Open Publication No. 2012-87587
U.S. Pat. No. 4,180,071

DISCLOSURE

Technical Problem

The present invention is conceived to solve these problems, and an object of the present invention is to provide to a filtering injection needle assembly for a syringe, wherein the filtering injection needle assembly blocks foreign substances introduced into the syringe and also adhered to an injection needle so that the filtering injection needle assembly may prevent ampoule fragments from being injected together with an injection liquid into a human body, thereby enhancing safety, and wherein the filtering injection needle assembly has various types of one-way valve means provided in a hub of the injection needle to further facilitate suction of the injection liquid, thereby improving user's convenience of use and thus maximizing merchantability and market competitiveness of a product.

Technical Solution

The present invention is achieved by a filtering injection needle assembly for a syringe, including an injection needle including a needle and a hub for supporting the needle and configured to be couplable to the syringe; and a cap configured to receive the needle and to be hermetically couplable to an outer periphery of the hub and including a filter, wherein the hub is formed with a through-hole for communication between an inside and an outside of the hub, and opening/closing of the through-hole is controlled by a one-way valve means.

Similarly, the present invention can be achieved by a filtering injection needle assembly for a syringe, including an injection needle including a needle and a hub for supporting the needle; a hollow connector assembled with the injection needle to couple the injection needle to the syringe; and a cap configured to receive the injection needle and to be hermetically coupled to an outer periphery of the connector and including a filter, wherein the connector is formed with a through-hole for communication between an inside and an outside of the connector, and opening/closing of the through-hole is controlled by a one-way valve means.

Here, the one-way valve means may be opened in response to coupling of the cap and may be closed in response to detachment of the cap. Alternatively, the one-way valve means may be opened in response to action of a negative pressure within the syringe and may be closed in response to action of a positive pressure within the syringe.

The one-way valve means opened or closed in response to the coupling or detachment of the cap preferably includes a resilient band having a circular cross-section and resiliently surrounding the though-hole to hermetically close the through-hole, a protrusion formed on an inner peripheral surface of the cap and brought into contact with and moving the resilient band in response to an axial movement of the cap, and a groove configured to return the resilient band to a location where the resilient band closes the through-hole.

Alternatively, the one-way valve means opened or closed in response to the coupling or detachment of the cap may include a resilient band resiliently surrounding the though-hole to hermetically close the through-hole, and a protrusion formed on the inner peripheral surface of the cap and brought into contact with and lifting the resilient band to create a gap between an inner peripheral surface of the resilient band and an outer peripheral surface of the hub in response to an axial movement of the cap.

Here, it is preferable that an contacting projection cooperating with the protrusion is protrudingly formed on an outer peripheral surface of the resilient band, or the protrusion is in the shape of a wedge configured to be inserted between the though-hole and the inner peripheral surface of the resilient band in response to the axial movement and to be formed with a flow hole.

Meanwhile, the one-way valve means opened or closed in response to the pressure within the syringe may be a well-known check valve comprising a sphere for selectively opening or closing the through-hole, or a well-known check valve comprising a resilient flap for selectively opening or closing the through-hole.

Alternatively, the one-way valve means opened or closed in response to the pressure within the syringe may include an inclined slit connected to the through-hole so that the slit is opened or closed by elastic self-deformation in sectional shape.

Advantageous Effects

The filtering injection needle assembly of the present invention can block foreign substances introduced into the syringe and also adhered to the injection needle so that the filtering injection needle assembly may prevent ampoule fragments from being injected together with the injection liquid into a human body, thereby enhancing safety, and the filtering injection needle assembly can have various types of one-way valve means provided in the hub of the injection needle to further facilitate suction of the injection liquid, thereby improving user's convenience of use and thus maximizing merchantability and market competitiveness of a product.

DESCRIPTION OF DRAWINGS

FIGS. 6 (a) and (b) are sectional views illustrating an operation of a first embodiment of a one-way valve means in the filtering injection needle assembly for the syringe according to the present invention.

FIGS. 8 (a) and (b) are sectional views illustrating an operation of the second embodiment of the one-way valve means in the filtering injection needle assembly for the syringe according to the present invention.

FIGS. 12 (a) and (b) are sectional views illustrating an operation of a sixth embodiment of the one-way valve means in the filtering injection needle assembly for the syringe according to the present invention.

FIGS. 13 (a) and (b) are sectional views illustrating an operation of a seventh embodiment of the one-way valve means in the filtering injection needle assembly for the syringe according to the present invention.

BEST MODE

Figure 4:
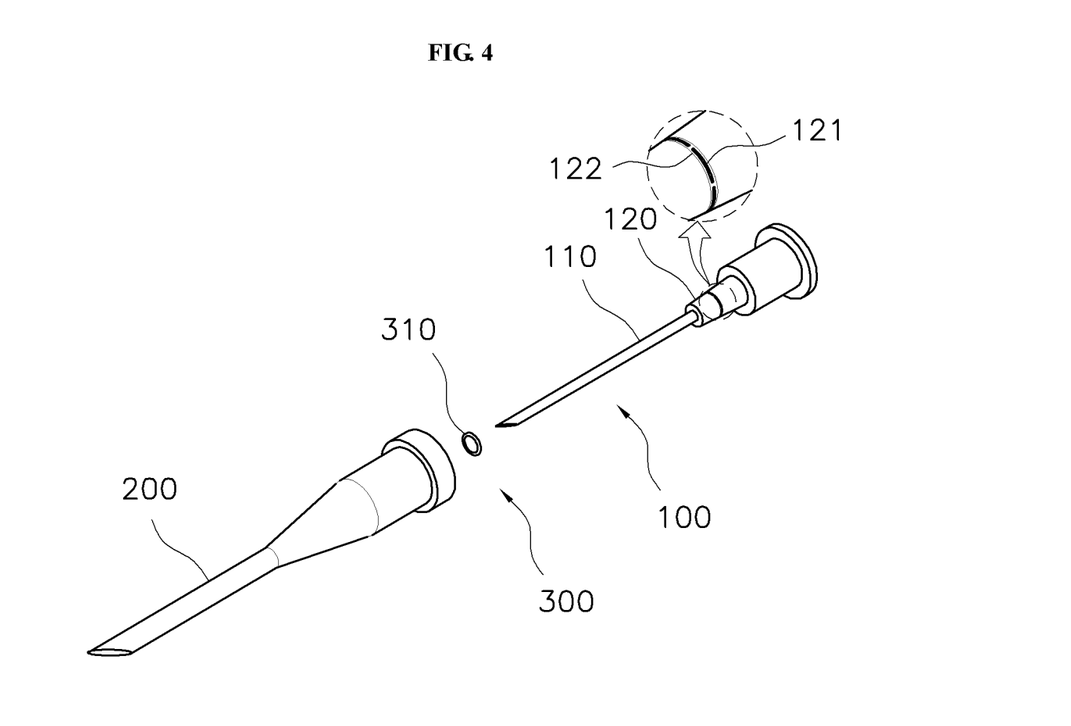
FIG. 4 is an exploded perspective view illustrating one example of a filtering injection needle assembly for a syringe according to the present invention.
Figure 5:
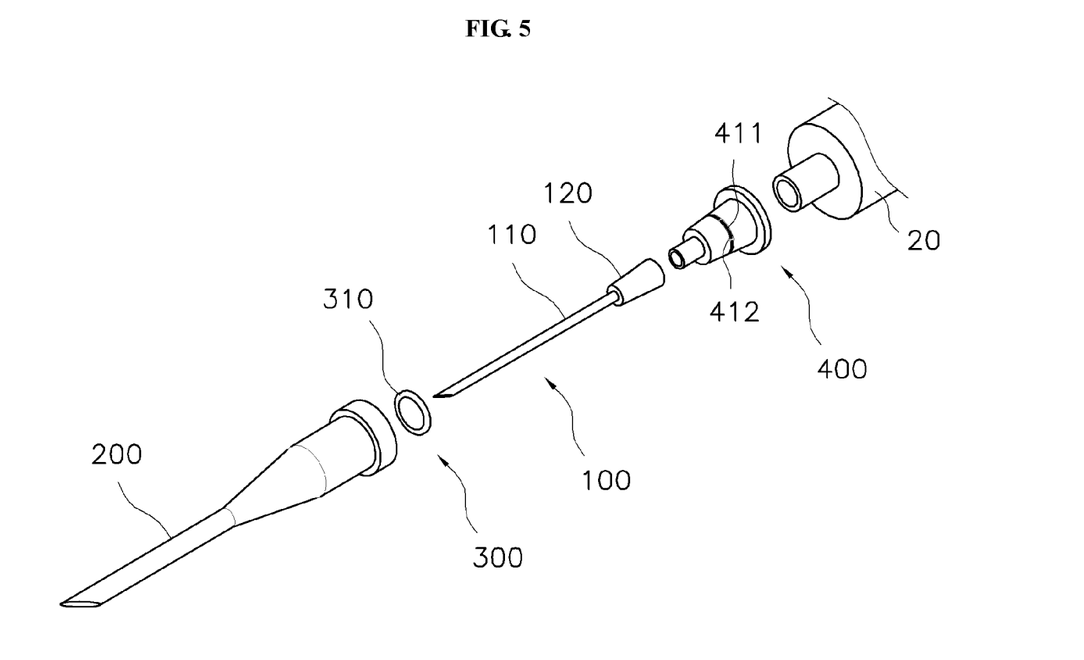
FIG. 5 is an exploded perspective view illustrating another example of the filtering injection needle assembly for the syringe according to the present invention.
Figure 6:
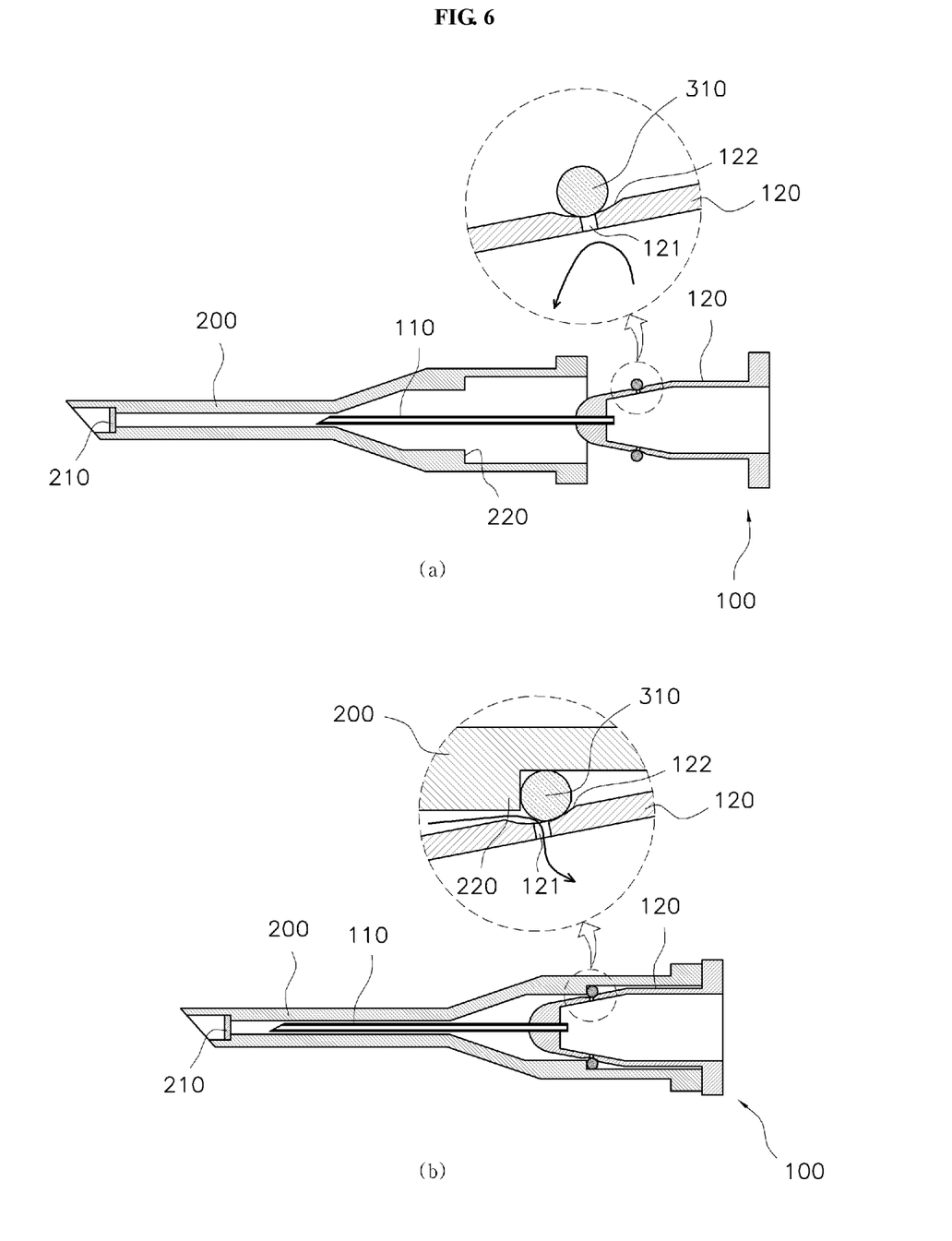

FIG. 4 is an exploded perspective view illustrating one example of a filtering injection needle assembly for a syringe according to the present invention, FIG. 5 is an exploded perspective view illustrating another example of the filtering injection needle assembly for the syringe according to the present invention, and FIGS. 6 (a) and (b) are sectional views illustrating an operation of a first embodiment of a one-way valve means in the filtering injection needle assembly for the syringe according to the present invention, wherein FIG. 6 (a) shows a closed state of the one-way valve means 300 and FIG. 6 (b) shows an opened state of the one-way valve means 300.

Figure 7:
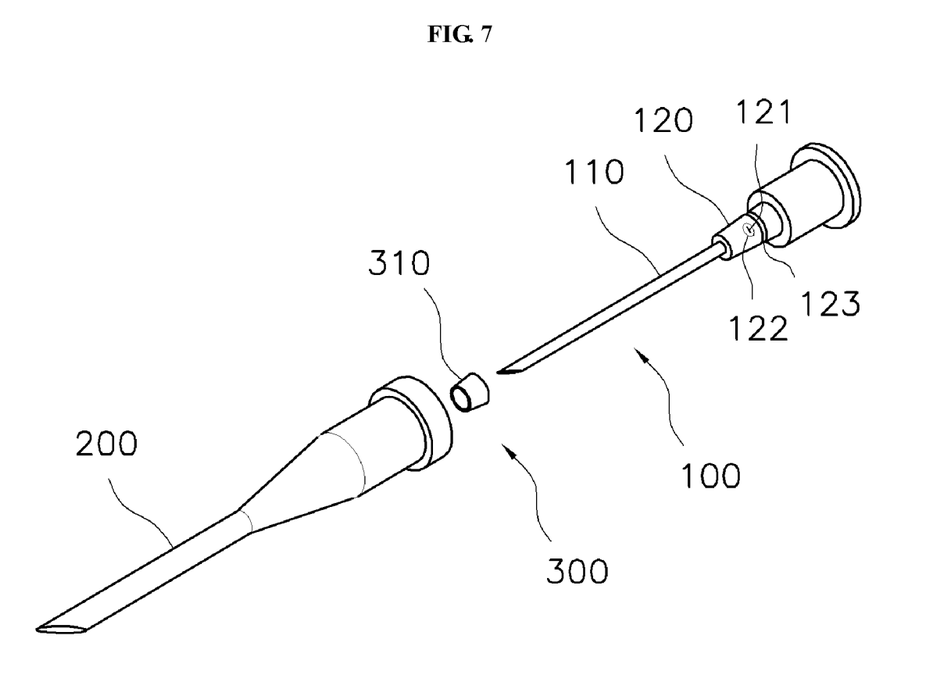
FIG. 7 is an exploded perspective view illustrating a second embodiment of the one-way valve means in the filtering injection needle assembly for the syringe according to the present invention.
Figure 8:
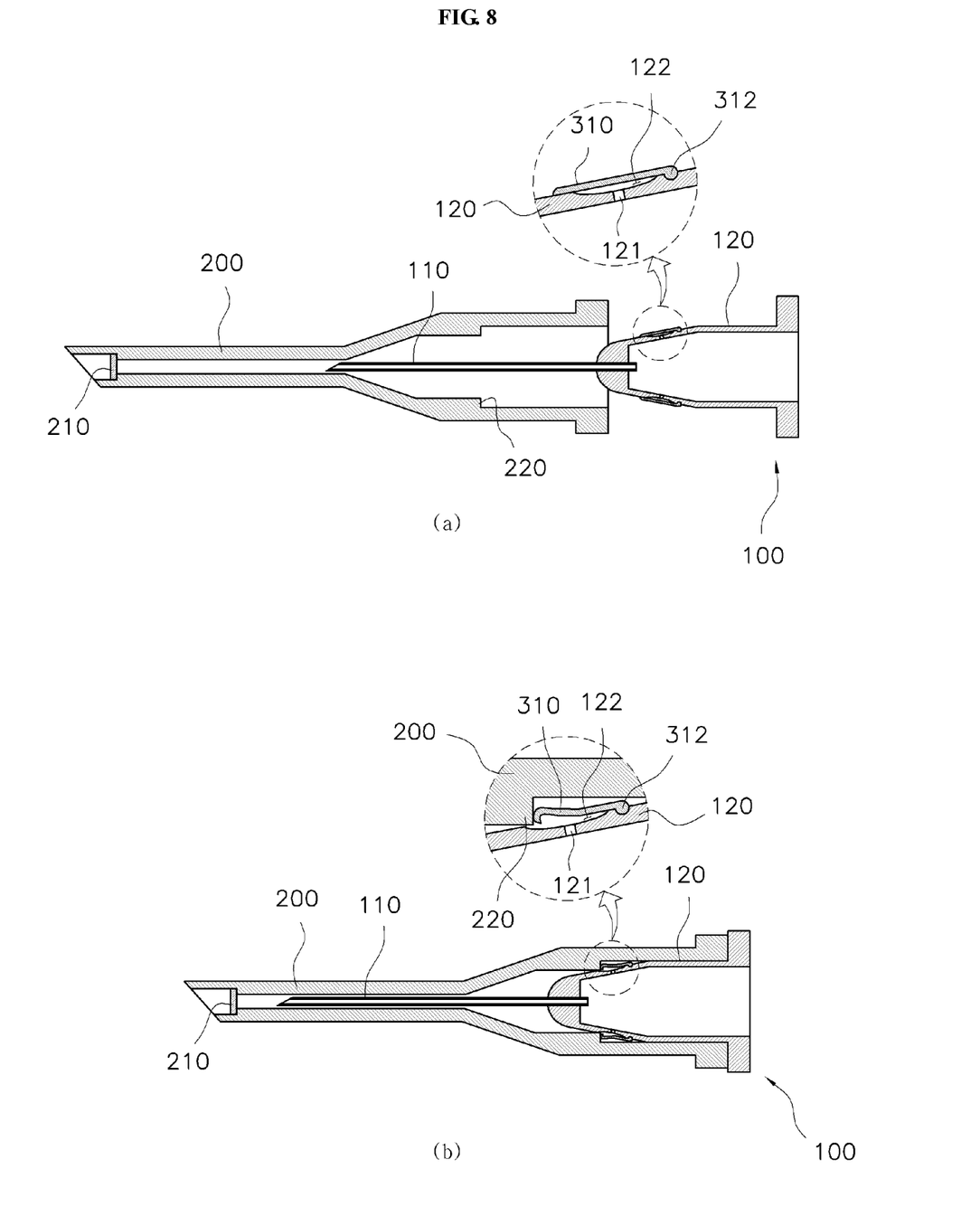

Moreover, FIG. 7 is an exploded perspective view illustrating a second embodiment of the one-way valve means in the filtering injection needle assembly for the syringe according to the present invention, and FIGS. 8 (a) and (b) are sectional views illustrating an operation of the second embodiment of the one-way valve means in the filtering injection needle assembly for the syringe according to the present invention, wherein FIG. 8 (a) shows a closed state of the one-way valve means 300 and FIG. 8 (b) shows an opened state of the one-way valve means 300.

Figure 9:
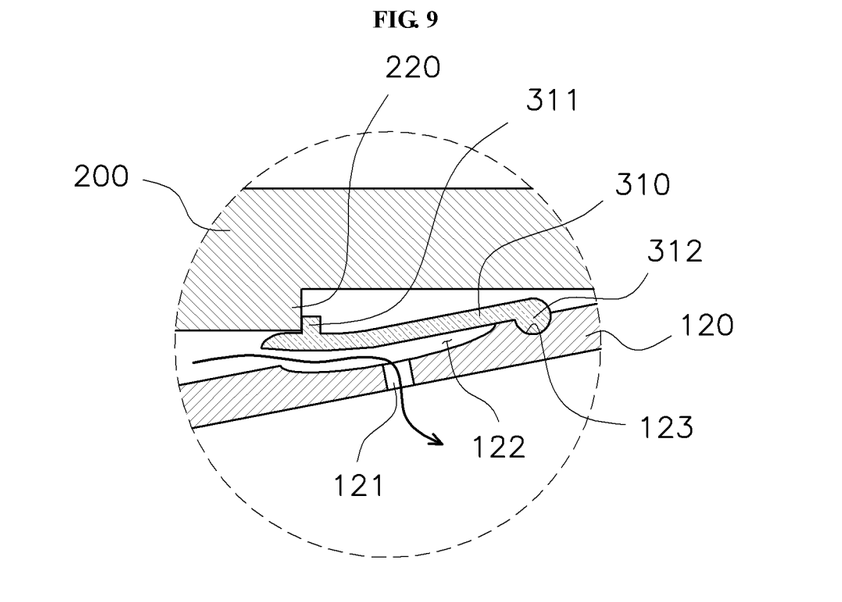
FIG. 9 is a sectional view illustrating a main portion of a third embodiment of the one-way valve means in the filtering injection needle assembly for the syringe according to the present invention.
Figure 10:
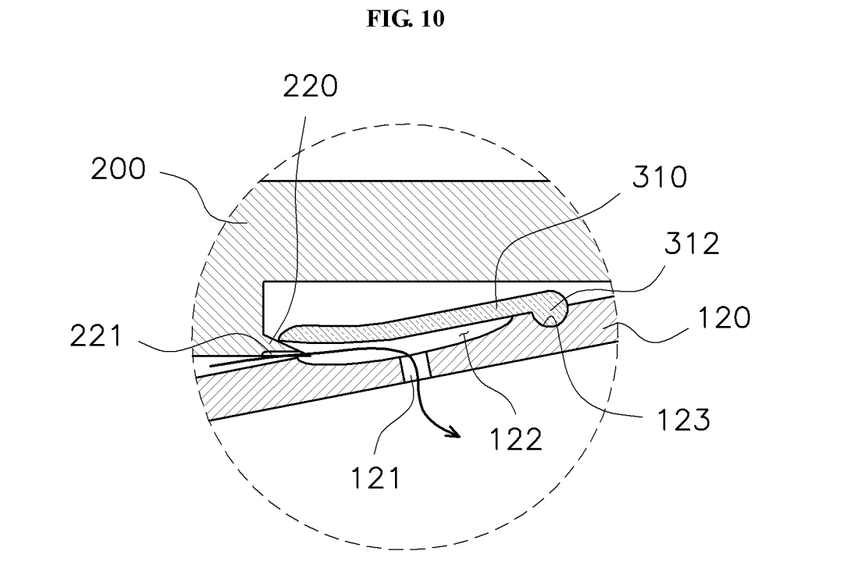
FIG. 10 is a sectional view illustrating a main portion of a fourth embodiment of the one-way valve means in the filtering injection needle assembly for the syringe according to the present invention.

Furthermore, FIG. 9 is a sectional view illustrating a main portion of a third embodiment of the one-way valve means in the filtering injection needle assembly for the syringe according to the present invention, and FIG. 10 is a sectional view illustrating a main portion of a fourth embodiment of the one-way valve means in the filtering injection needle assembly for the syringe according to the present invention, wherein both FIGS. 9 and 10 show states where the one-way valve means 300 is opened.

Figure 11:
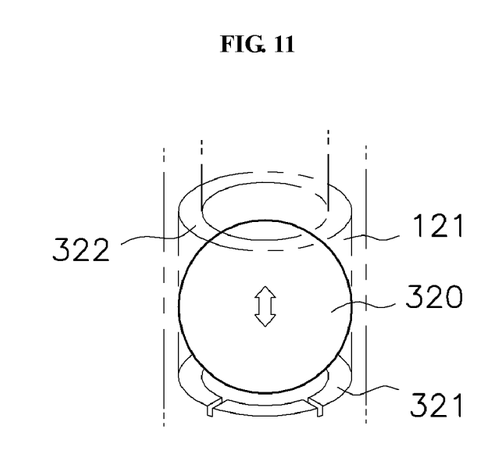
FIG. 11 is a perspective view illustrating a main portion of a fifth embodiment of the one-way valve means in the filtering injection needle assembly for the syringe according to the present invention.
Figure 12:
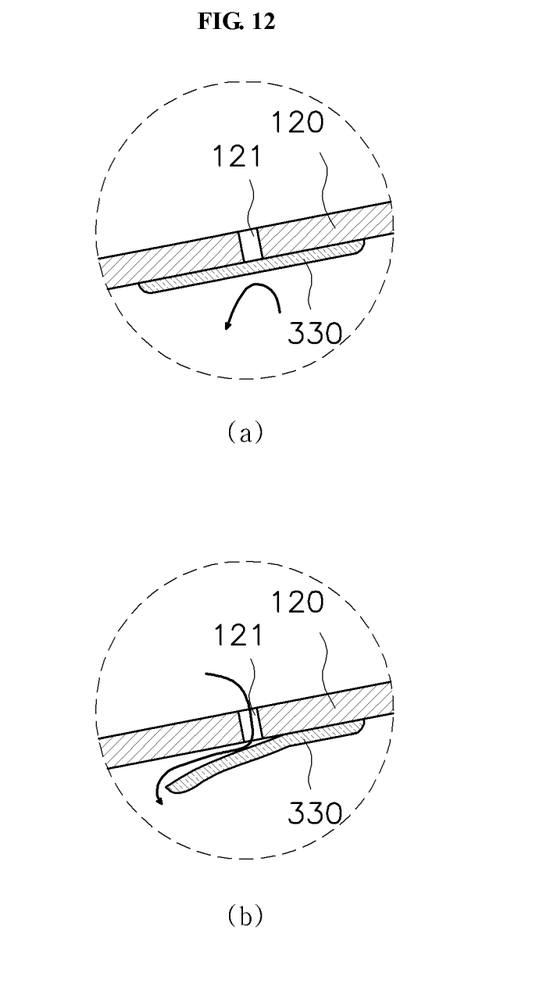

In addition, FIG. 11 is a perspective view illustrating a main portion of a fifth embodiment of the one-way valve means in the filtering injection needle assembly for the syringe according to the present invention, and FIGS. 12 (a) and (b) are sectional views illustrating an operation of a sixth embodiment of the one-way valve means in the filtering injection needle assembly for the syringe according to the present invention, wherein FIG. 12 (a) shows a closed state of the one-way valve means 300 and FIG. 12 (b) shows an opened state of the one-way valve means 300.

Figure 13:
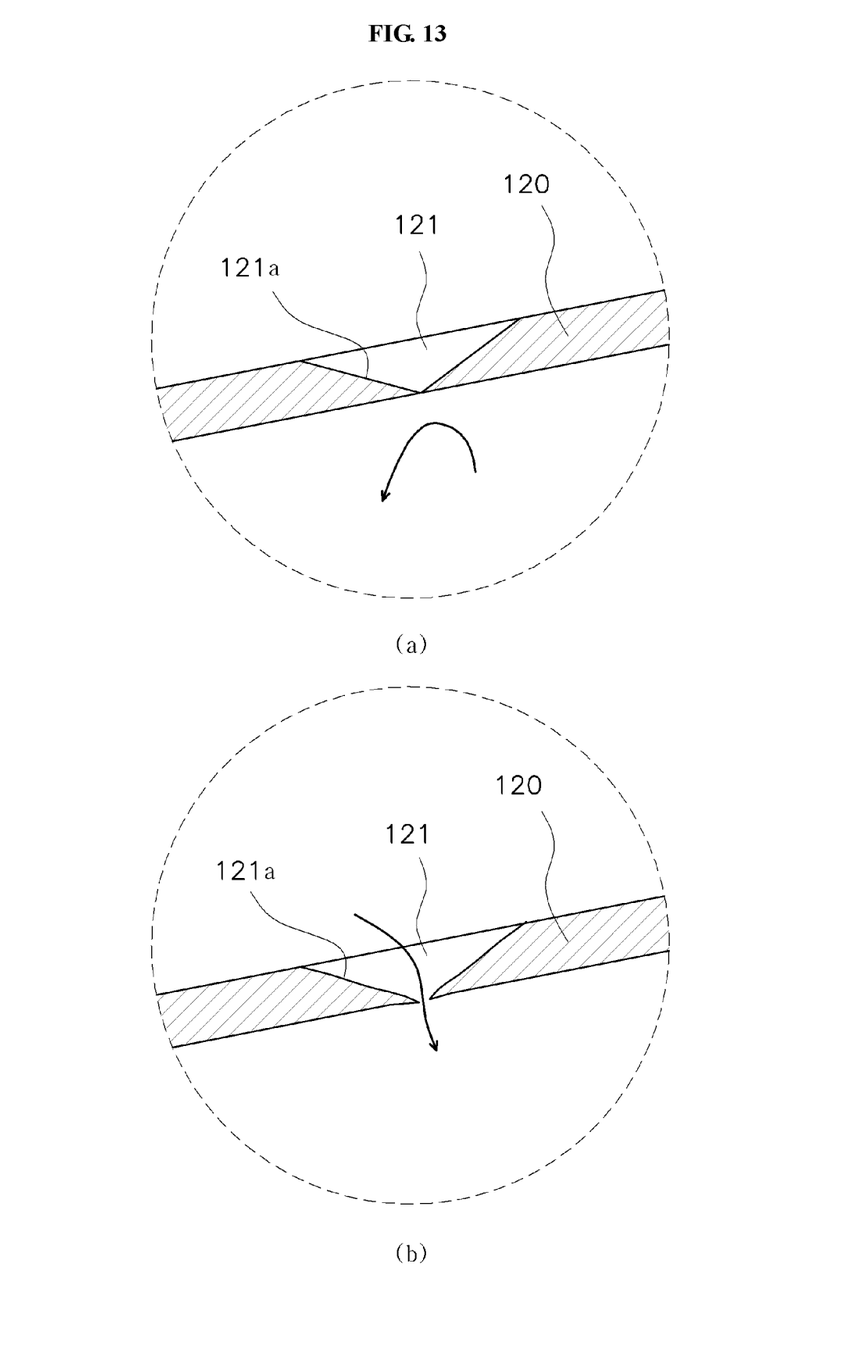

Finally, FIGS. 13 (a) and (b) are sectional views illustrating an operation of a seventh embodiment of the one-way valve means in the filtering injection needle assembly for the syringe according to the present invention, wherein FIG. 13 (a) shows a closed state of the one-way valve means 300 and FIG. 13 (b) shows an opened state of the one-way valve means 300.

As shown in FIGS. 4 to 13, the filtering injection needle assembly for the syringe according to the present invention is basically and technically characterized in that the one-way valve means 300 is additionally provided to an injection needle 100 consisting of a needle 110 and a hub 120 or to a connector 400 for assembling the injection needle 100 to a syringe so that upon suction of an injection liquid, the one-way valve means 300 is opened to allow the injection liquid passing through a filter 210 to be smoothly suctioned into a cylinder of the syringe, whereas upon injection of the injection liquid, the one-way valve means 300 is closed to allow the injection liquid to be injected into a patient's body through the needle 110.

Embodiments of the present invention will be described below in detail with reference to the accompanying drawings.

First of all, the filtering injection needle assembly for the syringe according to the present invention may be commonly applied to a conventional syringe (see FIG. 1) which basically consists of a cylinder for containing an injection liquid and a plunger provided to be movable forward and backward in an axial direction within the cylinder. There is no limitation on the shape or type of the syringe.

As shown in FIGS. 4 and 6, the filtering injection needle assembly for the syringe according to the present invention consists of the injection needle 100 including the needle 110 and the hub 120 for supporting the needle 110 and configured to be couplable to the syringe 20; and a cap 200 configured to receive the needle 110 and to be hermetically couplable to an outer periphery of the hub 120 and including the filter 210, wherein the hub 120 is formed with a through-hole 121 for communication between an inside and an outside of the hub 120, and opening/closing of the through-hole 121 is controlled by the one-way valve means 300.

In other words, the present invention mainly includes the injection needle 100 consisting of the needle 110 and the hub 120, the cap 200 including the filter 210, and the one-way valve means 300 for selectively opening or closing the through-hole 121 formed on the hub 120, and is coupled to a front end of the cylinder of the conventional syringe.

As shown in FIG. 5, the filtering injection needle assembly for the syringe according to the present invention may include the injection needle 100 consisting of the needle 110 and the hub 120 for supporting the needle 110; the hollow connector 400 assembled with the injection needle 100 to couple the injection needle 100 to the syringe 20; and the cap 200 configured to receive the injection needle 100 and to be hermetically coupled to an outer periphery of the connector 400 and including the filter 210, wherein the connector 400 may be formed with a through-hole 411 for communication between an inside and an outside of the connector 400, and opening/closing of the through-hole 411 may be controlled by the one-way valve means 300.

Since this configuration is substantially identical with the previously described configuration except that only the connector 400 is additionally provided, the through-hole 411 is formed on the connector 400 so that the one-way valve means 300 is placed at the through-hole 411 formed on the connector 400, and the cap 200 is coupled to the connector 400, substantially all of operations of this configuration are the same as those of the previously described configuration. Therefore, the configuration in which the through-hole 121 is formed on the hub 120 of the injection needle 100 will be described below by way of example with reference to FIGS. 4 and 6, and redundant descriptions in connection with FIG. 5 will be omitted.

The connector 400 is a hollow body including an inlet having a diameter for allowing assembly with the injection needle 100 and an outlet having a diameter for allowing assembly with the syringe (indicated by reference numeral 20 in FIG. 5), and is a connection body configured to assemble the injection needle 100 to the syringe 20.

When the connector 400 is used, there is an advantage in that the function of the present invention is performed even while using the injection needle 100 as it is without modifying.

First, the injection needle 100 includes the needle 110 which is typically a capillary tube made of a metal or synthetic resin material having high stiffness, and the hub 120 which is typically made of a synthetic resin material and supports a rear end of the needle 110 by being integrally injection-molded to surround the rear end of the needle 110.

The through-hole 121 is formed on the hub 120 such that the injection liquid may pass through the through-hole 121 between the inside and the outside of the hub 120.

It is preferable that one or more through-holes 121 are provided on one hub 120 and the plurality of the through-holes 121 are radially arranged.

The number and sizes of the through-holes 121 affect an operation force exerted by a user when the injection liquid is suctioned. As the number and sizes of the through-holes 121 are increased, the suction of the injection liquid becomes smoother. However, it will be apparent that the number and sizes of the through-holes 121 may be appropriately increased or decreased in consideration of convenience of manufacturing and the like.

Next, the cap 200 is a hollow pipe made of a metal or synthetic resin material, and accommodates the needle 110 and is resiliently coupled to the hub 120 while surrounding an outer peripheral surface of the hub 120 to keep a hermetical state. In particular, the filter 210 is provided at a tip of the cap in order to filter foreign substances contained in the injection liquid.

The filter 210 has a well-known structure.

Here, the one-way valve means 300, which will be described in detail later, is provided in the vicinity of the through-hole 121 or installed directly within the through-hole 121, so that the through-hole 121 is opened or closed by the one-way valve means 300.

In particular, it is preferable in the present invention that the opening or closing of the through-hole 121 by the one-way valve means 300 is controlled according to the following two conditions.

First, the one-way valve means 300 is opened as the cap 200 is coupled to the injection needle 100 and is closed as the cap 200 is detached therefrom. These operations correspond to the first to fourth embodiments described below.

Second, the one-way valve means 300 is opened in response to action of a negative pressure within the syringe and is closed in response to action of a positive pressure within the syringe. These operations correspond to the fifth to seventh embodiments described below.

Although the one-way valve means 300 has been described above in view of its functions, the one-way valve means 300 may be variously implemented in well-known configurations to perform such functions. Respective preferred embodiments of the present invention will be described as follows.

First Embodiment

In the present invention, as shown in FIGS. 4 and 6, the one-way valve means 300 includes a resilient band 310 having a circular cross-section and resiliently surrounding the though-hole 121 to hermetically close the through-hole 121, a protrusion 220 formed on an inner peripheral surface of the cap 200 and brought into contact with and moving the resilient band 310 in response to an axial movement of the cap 200, and a groove 122 configured to return the resilient band 310 to a location where the resilient band 310 closes the through-hole 121.

The groove 122 is formed around the entire periphery of the hub 120 to maintain the position of the resilient band 310.

In this case, when the injection needle 100 is not coupled with the cap 200 as shown in FIG. 6 (a), the resilient band 310 is introduced by an inclined surface of the groove 122 and placed at a center of the groove 122 to close the through-hole 121.

When the cap 200 is coupled to the injection needle 100 as shown in FIG. 6 (b), however, the protrusion 220 formed on the inner peripheral surface of the cap 200 moves the position of the resilient band 310 to open the through-hole 121.

Then, when the cap 200 is detached, the resilient band 310 which has been moved previously is returned to its original position by the inclined surface of the groove 122 and closes the through-hole 121 again as shown in FIG. 6 (a).

Meanwhile, in FIG. 5, a groove formed on the connector 400 is indicated by reference numeral 412.

Second Embodiment

In the present invention, as shown in FIGS. 7 and 8, it is preferable that the one-way valve means 300 includes a resilient band 310 resiliently surrounding the though-hole 121 to hermetically close the through-hole 121, and a protrusion 220 formed on the inner peripheral surface of the cap 200 and brought into contact with and lifting the resilient band 310 to create a gap between an inner peripheral surface of the resilient band 300 and the outer peripheral surface of the hub 120 in response to the axial movement of the cap 200.

As shown in FIGS. 7 and 8, it is preferable to concavely form the groove 122 around the through-hole 121, and the resilient band 310 is an annular band formed of a resilient material and covering the through-hole 121 as well as the groove 122.

With this configuration, when the cap 200 is not coupled to the injection needle 100, the through-hole 121 is kept in the closed state by the resilient band 310 as shown in FIG. 8 (a).

However, since the protrusion 220 is protrudingly formed on the inner peripheral surface of the cap 200, the coupling of the cap 200 to the injection needle 100 causes the protrusion 220 to come into contact with the resilient band 310 so that the resilient band 310 is bent and deformed as shown in FIG. 8 (b). As a result, the resilient band 310 is lifted to create the gap between the outer peripheral surface of the hub 120 and the inner peripheral surface of the resilient band 310, thereby switching the through-hole 121 to the opened state.

Of course, when the cap 200 is detached again, the shape of the resilient band 310 is resiliently restored to close the through-hole 121 again as shown in FIG. 8 (a).

It would be preferable that the resilient band 310 can be deformed but cannot be changed in position by protrudingly forming a fixing protrusion 312 on the inner peripheral surface of the resilient band 310 and concavely forming a fixing groove 123 on the outer peripheral surface of the hub 120 such that the fixing protrusion 312 may be accommodated and seated in the fixing groove 123.

Third Embodiment

The third embodiment is a variant of the second embodiment described above. As shown in FIG. 9, an contacting projection 311 cooperating with the protrusion 220 is protrudingly formed on an outer peripheral surface of the resilient band 310.

In other words, although the entire thickness of the resilient band 310 may be appropriately designed to cooperate with the protrusion 220 as in the second embodiment, the operation of the second embodiment described above may be performed more smoothly by separately providing the protruding contacting projection 311 on the resilient band 310 as in the third embodiment.

Fourth Embodiment

The fourth embodiment is also a variant of the second embodiment described above. As shown in FIG. 10, the protrusion 220 is in the shape of a wedge configured to be inserted between the through-hole 121 and the inner peripheral surface of the resilient band 310 in response to the axial movement and to be formed with a flow hole 221.

In other words, the protrusion 220 in the second or third embodiment comes into contact with the body itself or the contacting projection 311 of the resilient band 310 and lifts the resilient band 310 to create the gap, whereas the protrusion 220 in the fourth embodiment is formed in the wedge shape and snuggled between the outer peripheral surface of the hub 120 and the inner peripheral surface of the resilient band 310 to lift the resilient band 310.

To this end, it is preferable that a rear end of the protrusion 220 is formed in the shape of a sharply pointed wedge. And, it is preferable to further form the flow hole 221 on an inner peripheral surface of the protrusion 220 to allow the injection liquid to flow therethrough.

The flow hole 221 may be formed in the shape of a hollow having a circular cross-section or may be formed as a groove having a semicircular cross-section as illustrated in the figure.

Fifth Embodiment

In the present invention, the one-way valve means 300 is a well-known check valve including a sphere 320 which selectively opens or closes the through-hole 121, as shown in FIG. 11.

In the check valve including the sphere 320, contact seats 321 and 322 are formed on both sides of the movable sphere 320, wherein one contact seat 321 is cut out to allow the injection liquid to flow through a cut-out portion and the opposite contact seat 322 is configured to be brought into contact with an outer surface of the sphere 320 to keep a hermetic state.

As a result, when a negative pressure acts within the syringe, the sphere 320 is moved toward the cut-out contact seat 321 to allow the injection liquid to flow through the cut-out portion, whereas when a positive pressure acts within the syringe, the sphere 320 is moved toward the sealed contact seat 322 to keep the hermetic state, thereby blocking a stream of the injection liquid.

As such, the check valve including the sphere 320 may be installed inside or outside the hub 120 in order to open or close the through-hole 121, and may also be installed directly within the through-hole 121 as illustrated in the figure.

Sixth Embodiment

In the present invention, the one-way valve means 300 is a well-known check valve including a resilient flap 330 which selectively opens or closes the through-hole 121 as shown in FIG. 12.

The check valve including the resilient flap 330 is formed by fixing the resilient flap 330 formed of a resilient thin film to an inner surface of the through-hole 121, wherein the resilient flap may be undetachably secured to the inner surface of the hub 120 by means of fusing or a additional structural component.

As a result, when a negative pressure acts within the syringe, the resilient flap 330 is lifted to allow a flow of the injection liquid as shown in FIG. 12 (b). However, when a positive pressure acts within the syringe, the resilient flap 330 closes the through-hole 121 to block the flow of the injection liquid as shown in FIG. 12 (a).

Seventh Embodiment

In the present invention, as shown in FIG. 13, the one-way valve means 300 consists of an inclined slit 121a connected to the through-hole 121 so that the slit is opened or closed by elastic self-deformation in sectional shape.

In other words, the wing-shaped slit 121a which is cut out to have a minute gap is formed in the through-hole 121, whereby when a negative pressure acts within the syringe, the slit 121a is elastically deformed to open the through-hole 121 as shown in FIG. 13 (b) to allow a flow of the injection liquid. However, when a positive pressure acts within the syringe, the slit 121a is resiliently deformed to close the through-hole 121 as shown in FIG. 13 (a) to block a flow of the injection liquid.

The seventh embodiment has the function of the one-way valve means 300 by properly processing the shape of the through-hole 121 formed in the hub 120, and has advantages of a simple structure and easy manufacture.

Hereinafter, the operation of the present invention will be described below with reference to the figures.

In the present invention configured as described above, in a state where the cap 200 is coupled to the injection needle 100 when the filtering injection needle assembly has the configuration shown in FIG. 4, and in a state where the cap 200 is coupled to the connector 400 when the filtering injection needle assembly has the configuration shown in FIG. 5, the injection needle 100 and the cap 200 are put together into an ampoule and the plunger of the syringe is then retreated to suction a liquid medicine into the syringe.

If a tip of the cap 200 is shaped to be sharpened, it is also possible to stick the cap into a vial to suction a liquid medicine.

Foreign substances such as glass fragments of the ampoule and the like are filtered while the suctioned injection liquid passes through the filter 210 provided in the cap 200, and the injection liquid which has been introduced into the cap 200 is then smoothly suctioned into the syringe through the needle 110 as well as the opened through-hole 121.

In cases of the first to fourth embodiments, since the cap 200 has been coupled to the injection needle 100, the resilient band 310 is brought into contact with the protrusion 220 formed on the cap 200 and is then moved or self-deformed to open the through-hole 121. In cases of the fifth to seventh embodiments, the one-way valve means 300 is opened due to the negative pressure acting within the syringe.

Then, when the suction of the injection liquid is completed, the cap 200 is detached from the injection needle 100 or the connector 400, and the injection needle 100 is then inserted into a patient's body to inject the injection liquid.

In cases of the first to fourth embodiments, since the cap 200 has been detached from the injection needle 100, the resilient band 310 is returned to its original position or the shape of the resilient band is resiliently restored to close the through-hole 121. In cases of the fifth to seventh embodiments, the one-way valve means 300 is closed due to the positive pressure acting within the syringe.

As a result, the injection liquid can be injected into a patient's body only through the needle 110 without passing through the through-hole 121 or 411 formed in the hub 120 or the connector 400.

Therefore, the filtering injection needle assembly for the syringe according to the present invention can block foreign substances introduced into the syringe and also adhered to the injection needle so that the filtering injection needle assembly may prevent ampoule fragments from being injected together with the injection liquid into a human body, thereby enhancing safety.

In addition, the present invention has great advantages in that various types of one-way valve means are provided in the hub of the injection needle to further facilitate the suction of the injection liquid, thereby improving user's convenience of use and thus maximizing merchantability and market competitiveness of a product.

The foregoing embodiments are examples only for the purpose of specific illustration of the spirit of the present invention. The scope of the present invention is not limited to the embodiments or accompanying drawings.

[Explanation of Reference Numerals]

| | |
|---|---|
| 100: injection needle | 110: needle |
| 120: hub | 121, 411: through-hole |
| 121a: slit | 122, 412: groove |
| 123: fixing groove | 200: cap |
| 210: filter | 220: protrusion |
| 221: flow hole | 300: one-way valve means |
| 310: resilient band | 311: contacting projection |
| 312: fixing protrusion | 320: sphere |
| 321: cut-out contact seat | 322: sealed contact seat |
| 330: resilient flap | 400: connector |

The invention claimed is:

1. A filtering injection needle assembly for a syringe, comprising:
an injection needle including a needle and a hub for supporting the needle and configured to be couplable to the syringe; and
a cap configured to receive the needle and to be hermetically couplable to an outer periphery of the hub and including a filter,
wherein the hub is formed with a through-hole for communication between an inside and an outside of the hub, and opening/closing of the through-hole is controlled by a one-way valve means;
wherein the one-way valve means is opened in response to coupling of the cap and is closed in response to detachment of the cap.

2. The filtering injection needle assembly of claim 1, wherein the one-way valve means comprises a resilient band having a circular cross-section and resiliently surrounding the though-hole to hermetically close the through-hole, a protrusion formed on an inner peripheral surface of the cap and brought into contact with and moving the resilient band in response to an axial movement of the cap, and a groove configured to return the resilient band to a location where the resilient band closes the through-hole.

3. The filtering injection needle assembly of claim 1, wherein the one-way valve means comprises a resilient band resiliently surrounding the though-hole to hermetically close the through-hole, and a protrusion formed on an inner peripheral surface of the cap and brought into contact with and lifting the resilient band to create a gap between an inner peripheral surface of the resilient band and an outer peripheral surface of the hub in response to an axial movement of the cap.

4. The filtering injection needle assembly of claim 3, wherein a contacting projection cooperating with the protrusion is protrudingly formed on an outer peripheral surface of the resilient band.

5. The filtering injection needle assembly of claim 3, wherein the protrusion is in the shape of a wedge configured to be inserted between the though-hole and the inner peripheral surface of the resilient band in response to the axial movement and to be formed with a flow hole.

6. A filtering injection needle assembly for a syringe, comprising:
an injection needle including a needle and a hub for supporting the needle;
a hollow connector assembled with the injection needle to couple the injection needle to the syringe; and
a cap configured to receive the injection needle and to be hermetically coupled to an outer periphery of the connector and including a filter,
wherein the connector is formed with a through-hole for communication between an inside and an outside of the connector, and opening/closing of the through-hole is controlled by a one-way valve means;
wherein the one-way valve means is opened in response to coupling of the cap and is closed in response to detachment of the cap.

7. The filtering injection needle assembly of claim 6, wherein the one-way valve means comprises a resilient band having a circular cross-section and resiliently surrounding the though-hole to hermetically close the through-hole, a protrusion formed on an inner peripheral surface of the cap and brought into contact with and moving the resilient band in response to an axial movement of the cap, and a groove configured to return the resilient band to a location where the resilient band closes the through-hole.

8. The filtering injection needle assembly of claim 6, wherein the one-way valve means comprises a resilient band resiliently surrounding the though-hole to hermetically close the through-hole, and a protrusion formed on an inner peripheral surface of the cap and brought into contact with and lifting the resilient band to create a gap between an inner peripheral surface of the resilient band and an outer peripheral surface of the hub in response to an axial movement of the cap.

9. The filtering injection needle assembly of claim 8, wherein a contacting projection cooperating with the protrusion is protrudingly formed on an outer peripheral surface of the resilient band.

10. The filtering injection needle assembly of claim 8, wherein the protrusion is in the shape of a wedge configured to be inserted between the though-hole and the inner peripheral surface of the resilient band in response to the axial movement and to be formed with a flow hole.

* * * * *